(12) United States Patent
Sarge et al.

(10) Patent No.: US 6,508,804 B2
(45) Date of Patent: *Jan. 21, 2003

(54) CATHETER HAVING CONTINUOUS LATTICE AND COIL REINFORCEMENT

(75) Inventors: Jeffrey A. Sarge, Fremont, CA (US); Henry Nita, Redwood Shores, CA (US); Simon Ngoc Huu Nguyen, San Jose, CA (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/363,122

(22) Filed: Jul. 28, 1999

(65) Prior Publication Data

US 2001/0041881 A1 Nov. 15, 2001

(51) Int. Cl.[7] ............................................. A61M 25/00
(52) U.S. Cl. ...................................... 604/524; 604/526
(58) Field of Search ................................ 604/523, 524, 604/526, 527, 528, 529

(56) References Cited

U.S. PATENT DOCUMENTS

| | | | |
|---|---|---|---|
| 4,279,252 A | 7/1981 | Martin | 128/349 R |
| 4,323,071 A | 4/1982 | Simpson et al. | 128/343 |
| 4,425,919 A | 1/1984 | Alston, Jr. et al. | 128/658 |
| 4,444,186 A | 4/1984 | Wolvek et al. | 128/325 |
| 4,516,972 A | 5/1985 | Samson | 604/282 |
| 4,563,181 A | 1/1986 | Wijayarathna et al. | 604/280 |
| 4,571,240 A | 2/1986 | Samson et al. | 604/96 |
| 4,636,346 A | 1/1987 | Gold et al. | 264/139 |
| 4,739,768 A | 4/1988 | Engelson | 128/658 |
| 4,817,613 A | 4/1989 | Jaraczewski et al. | 128/658 |
| 4,863,442 A | 9/1989 | DeMello et al. | 604/282 |
| 4,886,506 A | 12/1989 | Lovgren et al. | 604/280 |
| 4,898,591 A | 2/1990 | Jang et al. | 604/282 |
| 4,925,710 A | 5/1990 | Buck et al. | 428/34.5 |
| 4,990,143 A | 2/1991 | Sheridan | 604/282 |
| 5,017,259 A | 5/1991 | Kohsai | 156/294 |
| 5,019,057 A | 5/1991 | Truckai | 604/282 |
| 5,037,404 A | 8/1991 | Gold et al. | 604/282 |
| 5,057,092 A | 10/1991 | Webster, Jr. | 604/282 |
| 5,078,702 A | 1/1992 | Pomeranz | 604/280 |
| 5,103,543 A | 4/1992 | Hodgson | 29/173 |
| 5,176,660 A | 1/1993 | Truckai | 604/282 |
| 5,221,270 A | 6/1993 | Parker | 604/282 |
| 5,234,416 A | 8/1993 | Macaulay et al. | 604/282 |
| 5,251,640 A | 10/1993 | Osborne | 128/772 |

(List continued on next page.)

FOREIGN PATENT DOCUMENTS

WO   WO 98/56448   12/1998

*Primary Examiner*—Brian L. Casler
*Assistant Examiner*—Kevin C. Sirmons
(74) *Attorney, Agent, or Firm*—Crompton, Seager & Tufte, LLC

(57) ABSTRACT

A reinforced intravascular catheter adapted for use in performing minimally invasive medical procedures. A catheter, in accordance with the present invention, comprising an inner tubular member having an outer surface, a proximal end, a distal end, and a lumen extending therethrough. The catheter further including a support member overlaying the inner tubular member and conforming to the outer surface thereof, the support member including at least one filament forming a plurality of turns. The support member further including at least one multi-layered portion having a first layer and a plurality of additional layers, each layer comprising a plurality of turns formed by at least one filament, the plurality of additional layers each overlaying at least the first layer. The catheter also including an outer layer overlaying both the support member and the inner tubular member. A method of fabricating a catheter in accordance with the present invention is also disclosed.

21 Claims, 3 Drawing Sheets

U.S. PATENT DOCUMENTS

| | | | |
|---|---|---|---|
| 5,254,107 A | 10/1993 | Soltesz | 604/282 |
| 5,279,596 A | 1/1994 | Castaneda et al. | 604/282 |
| 5,295,978 A | 3/1994 | Fan et al. | 604/265 |
| 5,300,048 A | 4/1994 | Drewes, Jr. et al. | 604/280 |
| 5,312,356 A | 5/1994 | Engelson et al. | 604/164 |
| 5,334,166 A | 8/1994 | Palestrant | 604/265 |
| 5,399,164 A | 3/1995 | Snoke et al. | 604/95 |
| 5,441,489 A | 8/1995 | Utsumi et al. | 604/280 |
| 5,445,624 A | 8/1995 | Jimenez | 604/280 |
| 5,454,795 A | 10/1995 | Samson | 604/282 |
| 5,478,330 A | 12/1995 | Imran et al. | 604/282 |
| 5,496,292 A | 3/1996 | Burnham | 604/282 |
| 5,538,513 A | 7/1996 | Okajima | 604/282 |
| 5,542,924 A | 8/1996 | Snoke et al. | 604/95 |
| 5,554,139 A | 9/1996 | Okajima | 604/282 |
| 5,569,220 A | 10/1996 | Webster, Jr. | 604/282 |
| 5,599,326 A | 2/1997 | Carter | 604/282 |
| 5,658,264 A | 8/1997 | Samson | 604/282 |
| 5,662,622 A | 9/1997 | Gore et al. | 604/282 |
| 5,676,659 A | 10/1997 | McGurk | 604/282 |
| 5,695,483 A | 12/1997 | Samson | 604/282 |
| 5,702,373 A | 12/1997 | Samson | 604/282 |
| 5,711,909 A | 1/1998 | Gore et al. | 264/320 |
| 5,733,400 A | 3/1998 | Gore et al. | 156/158 |
| 5,755,704 A | 5/1998 | Lunn | 604/282 |
| 5,769,830 A | 6/1998 | Parker | 604/282 |
| 5,782,811 A | 7/1998 | Samson et al. | 604/282 |
| 5,785,685 A * | 7/1998 | Kugler et al. | 604/96 |
| 5,792,124 A * | 8/1998 | Horrigan et al. | 604/282 |
| 5,795,341 A | 8/1998 | Samson | 604/282 |
| 5,811,043 A * | 9/1998 | Horrigan et al. | 264/138 |
| 5,836,925 A | 11/1998 | Soltesz | 604/280 |
| 5,851,203 A | 12/1998 | van Muiden | 604/282 |
| 5,853,400 A | 12/1998 | Samson | 604/282 |
| 5,860,963 A | 1/1999 | Azam et al. | 604/280 |
| 5,897,567 A * | 4/1999 | Ressemann et al. | 606/159 |
| 5,906,605 A | 5/1999 | Coxum | 604/525 |
| 5,951,539 A * | 9/1999 | Nita et al. | 604/526 |
| 5,957,842 A * | 9/1999 | Littmann et al. | 600/381 |
| 5,960,796 A * | 10/1999 | Sung et al. | 128/897 |

\* cited by examiner

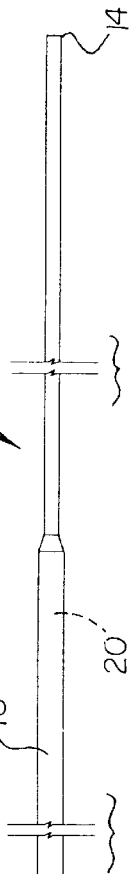
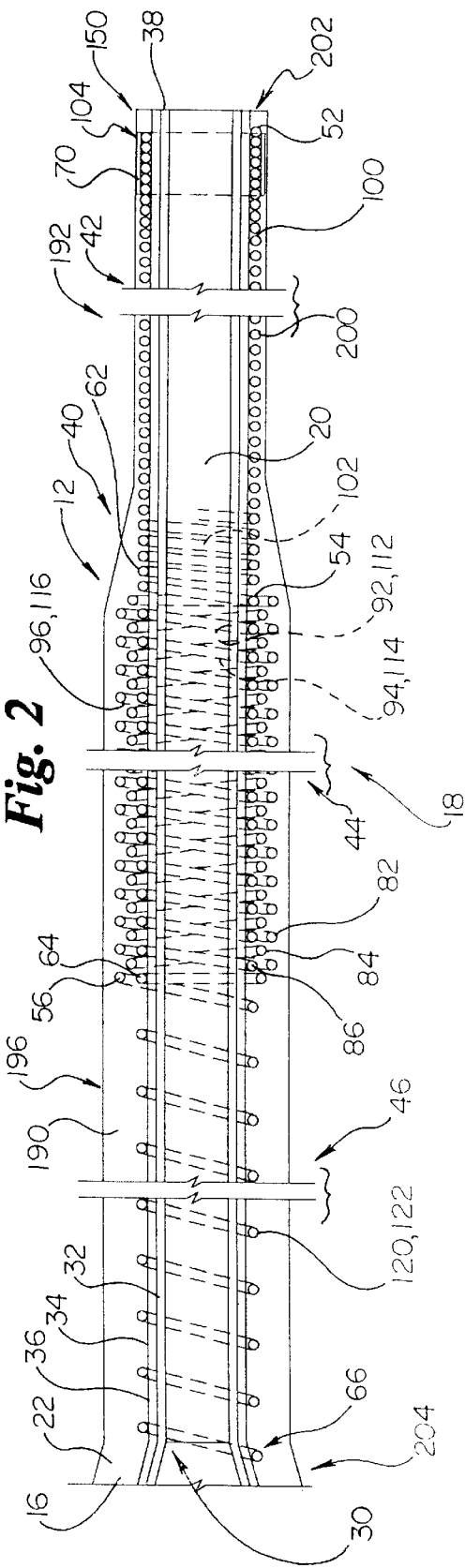

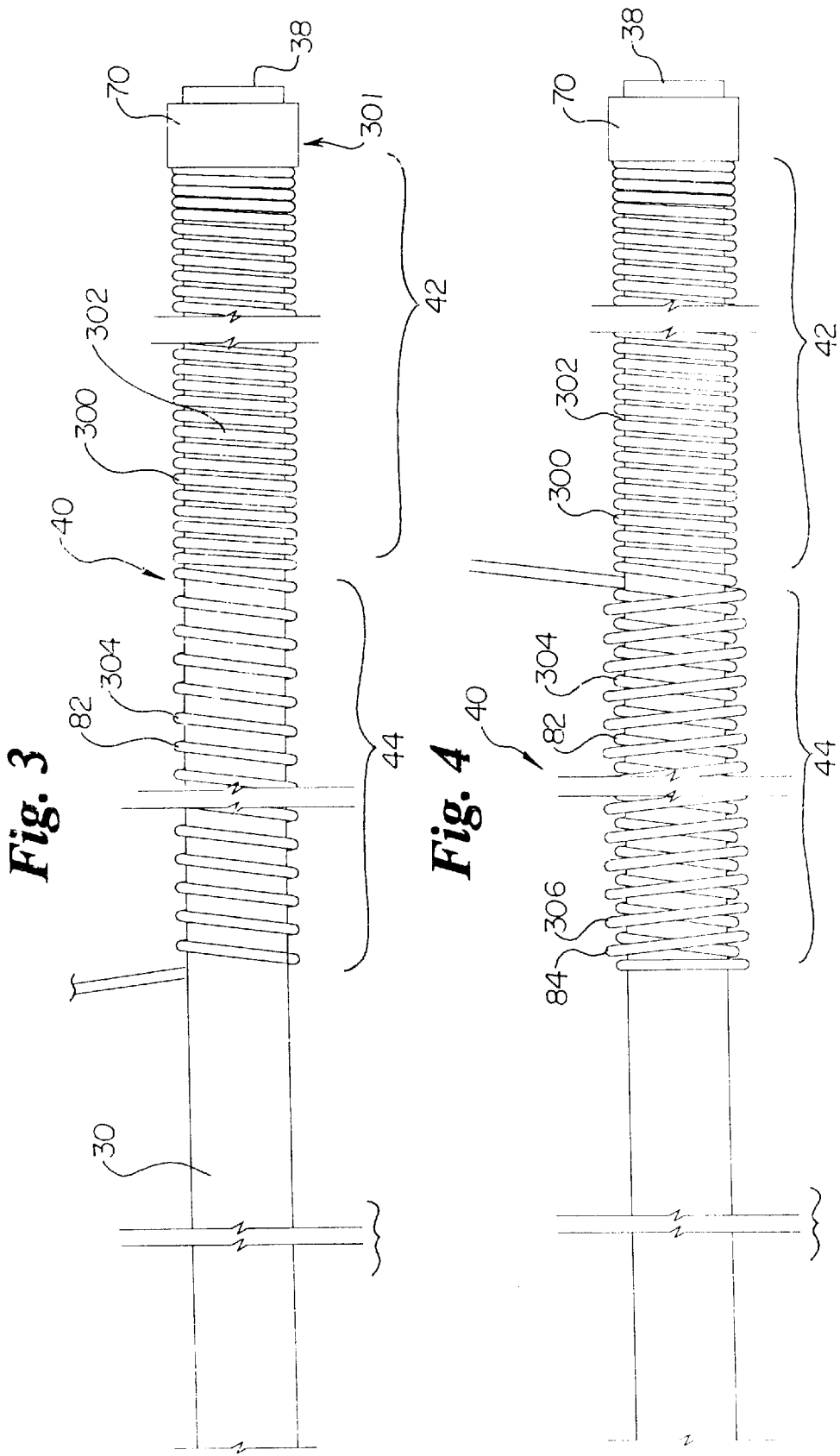

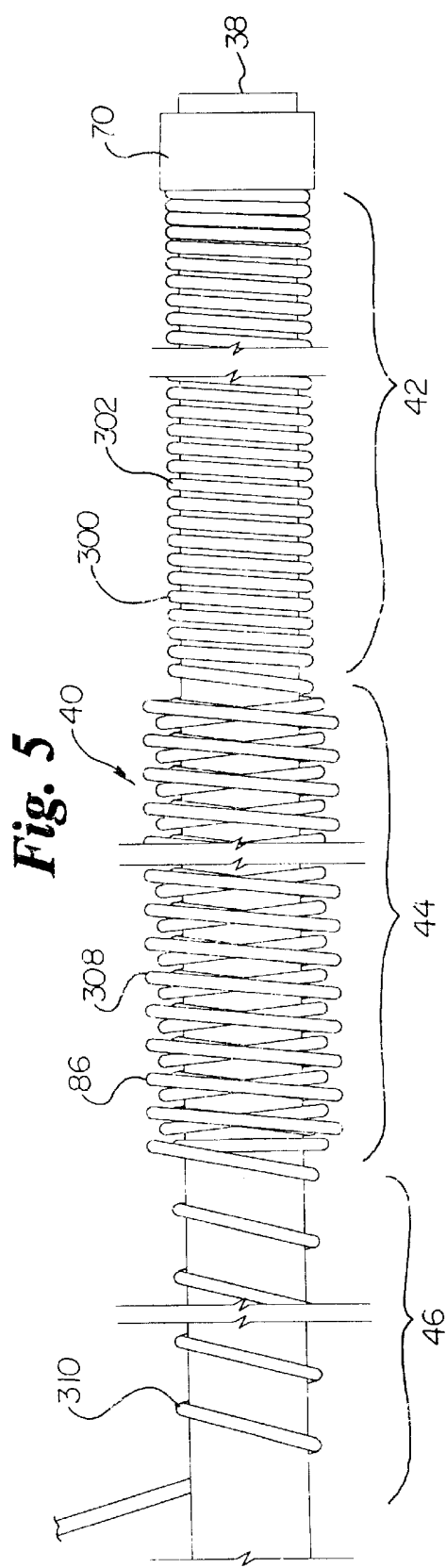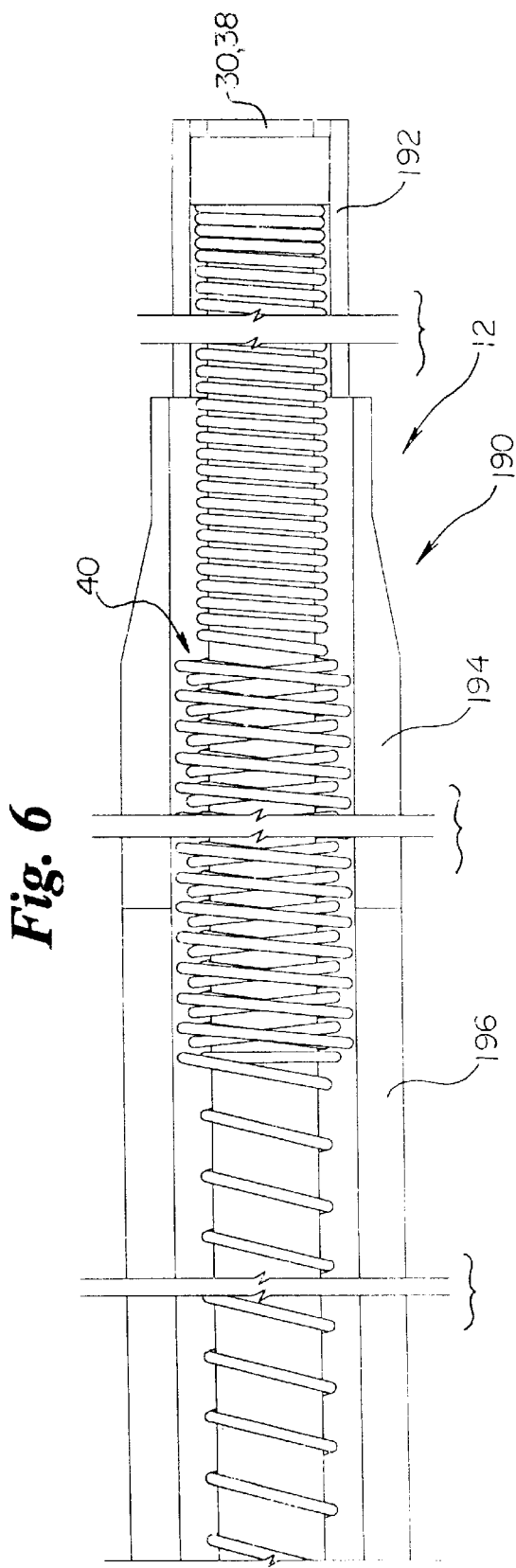

CATHETER HAVING CONTINUOUS LATTICE AND COIL REINFORCEMENT

FIELD OF THE INVENTION

The present invention relates generally to catheters for performing medical procedures. More particularly, the present invention relates to reinforced intravascular catheters.

BACKGROUND OF THE INVENTION

Intravascular catheters are currently utilized in a wide variety of minimally invasive medical procedures. Generally, an intravascular catheter enables a physician to remotely perform a medical procedure by inserting the catheter into the vascular system of the patient at a location that is easily accessible and thereafter navigating the catheter to the desired target site. By this method, virtually any target site in the patient's vascular system may be remotely accessed, including the coronary, cerebral, and peripheral vasculature.

Typically, the catheter enters the patient's vasculature at a convenient location such as a blood vessel in the neck or near the groin. Once the distal portion of the catheter has entered the patient's vascular system, the physician may urge the distal tip forward by applying longitudinal forces to the proximal portion of the catheter. For the catheter to effectively communicate these longitudinal forces, it is desirable that the catheter have a high level of pushability and kink resistance.

Frequently, the path taken by a catheter through the vascular system is tortuous, requiring the catheter to change direction frequently. It may also be necessary for the catheter to double back on itself. Physicians often apply torsional forces to the proximal portion of the catheter to aid in steering the catheter. To facilitate the steering process, it is desirable that an intravascular catheter have a relatively high level of torquability. Furthermore, in order for the catheter to conform to a patient's tortuous vascular system, it is desirable that intravascular catheters be very flexible.

The distance between the access site and the target site is often in excess of 100 cm. The inside diameter of the vasculature at the access site is often less than 5 mm. In light of the geometry of the patient's body, it is desirable to combine the features of torqueabity, pushability, and flexibility into a catheter which is relatively long and has a relatively small diameter.

Ideally, the distal end of an intravascular catheter will be adapted to reduce the probability that the vascular tissue will be damaged as the catheter is progressed through the vascular system. This is sometimes accomplished by bonding or welding a relatively soft tip member to the distal end of an intravascular catheter.

After the intravascular catheter has been navigated through the patient's vascular system so that its distal end is adjacent the target site, the catheter may be used for various diagnostic and/or therapeutic purposes. One example of a diagnostic use for an intravascular catheter is the delivery of radiopaque contrast solution to enhance fluoroscopic visualization. In this application, the intravascular catheter provides a fluid path leading from a location outside the body to a desired location inside the body of a patient. In order to maintain a fluid path, it is desirable that intravascular catheters be sufficiently resistant to kinking. In addition, because such fluids are delivered under pressure, it is also desirable that intravascular catheters be sufficiently resistant to bursting or leaking.

One useful therapeutic application of intravascular catheters is the treatment of intracranial aneurysms in the brain. Approximately 25,000 intracranial aneurysms rupture each year in North America. An aneurysm which is likely to rupture, or one which has already ruptured, may be treated by delivering an embolic device or agent to the interior of the aneurysm. The embolic device or agent encourages the formation of a thrombus inside the aneurysm. The formation of a thrombus reduces the probability that an aneurysm will rupture. The formation of a thrombus also reduces the probability that a previously ruptured aneurysm will re-bleed. Thrombus agents which may be used include liquid thrombus agents such as cyanocrylate, and granulated thrombus agents such as polyvinyl alcohol. An additional type of thrombus agent which is frequently used is a tiny coil. Any of the thrombus agents described above may be delivered using an intravascular catheter.

When treating an aneurysm with the aid of an intravascular catheter, the catheter tip is typically positioned proximate the aneurysm site. The thrombus agent is then urged through the lumen of the intravascular catheter and introduced into the aneurysm. Shortly after the thrombus agent is placed in the aneurysm, a thrombus forms in the aneurysm and is shortly thereafter complemented with a collagenous material which significantly lessens the potential for aneurysm rupture. It is desirable that the lumen of the catheter provides a path for delivering embolic devices to an aneurysm. To this end, it is desirable that the pathway through the catheter have a low friction surface.

The blood vessels in the brain frequently have an inside diameter of less than 3 mm. Accordingly, it is desirable that intravascular catheters intended for use in these blood vessels have an outside diameter which allows the catheter to be easily accommodated by the blood vessel. The path of the vasculature inside the brain is highly tortuous, and the blood vessels are relatively fragile. Accordingly, it is desirable that distal portion of a catheter for use in the brain be adapted to follow the highly torturous path of the neurological vasculature.

As described above, it is desirable to combine a number of performance features in an intravascular catheter. It is desirable that the catheter have a relatively high level of pushability and torqueability, particularly near its proximal end. It is also desirable that a catheter be relatively flexible, particularly near its distal end. The need for this combination of performance features is sometimes addressed by building a catheter which has two or more discrete tubular members having different performance characteristics. For example, a relatively flexible distal section may be bonded to a relatively rigid proximal section. When a catheter is formed from two or more discrete tubular members, it is necessary to form a bond between the distal end of one tubular member and the proximal end of another tubular member.

SUMMARY OF THE INVENTION

The present invention relates generally to catheters for performing medical procedures. More particularly, the present invention relates to reinforced intravascular catheters. A catheter in accordance with the present invention includes an elongate shaft. A hub may be fixed to the proximal end of the elongate shaft. The elongate shaft is comprised of an inner tubular member having a first layer, a second layer, an outer surface, and a distal end.

A support member overlies at least a portion of the inner tubular member and conforms to the surface thereof. The support member has a first portion, a second portion, and a third portion. The first portion, second portion, and third portion each have a distal end and a proximal end. The first portion of the support member being disposed proximate the distal end of the inner tubular member. The first portion of the support member is comprised of at least one filament which is circumferentially disposed about the inner tubular member in a helical manner. The at least one filament generally conforms to the shape of the outer surface of the inner tubular member and forms a plurality of turns.

In a presently preferred embodiment, a ring is circumferentially disposed about the outer surface of the inner tubular member proximate the distal end thereof. In a presently preferred embodiment, the ring is comprised of a radiopaque material. In this presently preferred embodiment, the ring produces a relatively bright image on a fluoroscopy screen during a medical procedure. This relatively bright image aids the user of the catheter in determining the location of the distal end of the elongate shaft.

In one embodiment of the present invention, a distal portion of the at least one filament is disposed between the outer surface of the inner tubular member and the ring. Placing the distal portion of the filament in this position has the advantage of retaining the distal portion of the filament while the remainder of the filament is wound around the inner tubular member.

The second portion of the support member is circumferentially disposed about the inner tubular member, with its distal end proximate the proximal end of the first portion of the support member. In one embodiment of the present invention, the second portion of the support member is comprised of a lattice structure having a first layer, a second layer, and a third layer. Each layer being comprised of a plurality of turns, formed by at least one filament.

The third portion of the support member is comprised of a plurality of turns formed by at least one filament. In a presently preferred embodiment, the filaments forming the support member are all coextensive.

In a presently preferred embodiment, the elongate shaft includes a flare disposed proximate the proximal end thereof. The hub may be formed over the proximal end of the elongate shaft. In a presently preferred embodiment, the hub is formed using an insert molding process. In this presently preferred embodiment, the single filament includes a distal end and a proximal end. In this presently preferred embodiment, it is unlikely that the distal end of the filament will protrude through the outer layer of the catheter since the distal portion of the filament is retained by a ring, as described above. Likewise, it is unlikely that the proximal end of the filament will protrude from the catheter since a hub is disposed over the proximal end of the elongate shaft.

An outer layer overlays both the support member, and the inner tubular member. In a presently preferred embodiment, the material of the outer layer fills any interstitial spaces in the support member. Also in a presently preferred embodiment, the outer layer is comprised of a distal portion, a middle portion, and a proximal portion.

In one embodiment of the present invention, the proximal end of the distal portion of the outer layer is fused to the distal end of the middle portion thereof. Likewise, the proximal end of the middle portion of the outer layer is fused to the distal end of the proximal portion. In this presently preferred embodiment, the distal portion, the middle portion, and the proximal portion combine to form an outer layer which is substantially continuous.

In one aspect of the present invention, the outer diameter of the proximal portion of the outer layer is large enough to substantially cover the layers of the second portion of the support member. Likewise, in another aspect of the present invention, the outer diameter of the distal portion of the outer layer is large enough to substantially cover the first portion of the support member. In a presently preferred embodiment, the outer diameter of the distal portion of the outer layer is smaller than the outer diameter of the proximal portion of the outer layer. It may be appreciated that the single layer construction of the first portion of the support member facilitates having an outer diameter of the distal portion which is smaller than the outer diameter of the proximal portion.

In one embodiment of the present invention, the plurality of turns forming the first portion of the support member are disposed at a first pitch. Also in this embodiment, the turns of the second portion of the support member are disposed at a second pitch different than the first pitch. Finally, in this embodiment, the turns of the third portion of the support member are disposed at a third pitch. In a presently preferred embodiment, the pitches of the first, second, and third portions of the support member may be selected to impart desired performance characteristics upon the catheter. For example, the third pitch may be relatively coarse so that it does not hinder the formation of a flare at the proximal end of the elongate shaft.

In a presently preferred embodiment, the distal end of the first portion of the support member is disposed proximate the distal end of the elongate shaft. An atraumatic tip is formed from the inner tubular member and the outer layer. In this presently preferred embodiment, the atraumatic tip is disposed distally of the distal portion of the first portion of the support member. In this presently preferred embodiment, the atraumatic tip has a level of flexibility which makes it unlikely to damage the blood vessels of a patient.

BRIEF DESCRIPTION OF THE DRAWINGS

FIG. 1 is a plan view of a catheter in accordance with an exemplary embodiment of the present invention;

FIG. 2 is a cross-sectional plan view of an elongate shaft in accordance with an exemplary embodiment of the present invention;

FIG. 3 is a plan view of an assembly including an inner tubular member and a filament in accordance with an exemplary embodiment of the present invention, the filament being circumferentially disposed about the inner tubular member following a generally helical path and forming a plurality of turns comprising a support member;

FIG. 4 is a plan view of the assembly of FIG. 3, to which a second layer has been added to a portion of the support member to form a lattice;

FIG. 5 is a plan view of the assembly of FIG. 4, to which a third layer has been added to a portion of the support member; and FIG. 6 is a plan view of the assembly of FIG. 5, in which a plurality of portions forming an outer layer are circumferentially disposed over the support member and the inner tubular member.

DETAILED DESCRIPTION OF THE INVENTION

The following detailed description should be read with reference to the drawings, in which like elements in different drawings are numbered identically. The drawings, which are not necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

FIG. 1 is a plan view of a catheter 10 in accordance with the present invention. Catheter 10 includes an elongate shaft 12 having a distal end 14, a proximal end 16, an outer surface 18, and a lumen 20 extending therethrough. Catheter 10 further includes a hub 26 and a strain relief 28 disposed proximate proximal end 16 of elongate shaft 12. Hub 26 and strain relief 28 enable a physician to connect other devices to catheter 10. Hub 26 and strain relief 28 also provide a convenient place for a physician to apply longitudinal or rotational forces in order to manipulate catheter 10.

FIG. 2 is a cross-sectional plan view of elongate shaft 12 of catheter 10. Elongate shaft 12 is comprised of an inner tubular member 30 having a first layer 32, a second layer 34, an outer surface 36, and a distal end 38. In a presently preferred embodiment, first layer 32 of inner tubular member 30 is comprised of PTFE (polytetrafluoroethylene). PTFE is a preferred material because it creates a smooth, low-friction surface for the passage of other devices or fluids through the catheter. Also in a presently preferred embodiment, second layer 34 of inner tubular member 30 is comprised of polyether block amide (PEBA). Polyether block amide is commercially available from Atochem Polymers of Birdsboro, Pa., under the trade name PEBAX. Those of skill in the art will appreciate that inner tubular member 30 may be comprised of a single layer or a plurality of layers without deviating from the spirit and scope of the present invention. Those of skill in the art will appreciate that other materials may be suitable for the layer(s) of inner tubular member 30. Examples of materials suitable in some applications include polyolefins, polyamides, and polyimides.

A support member 40 overlies inner tubular member 30 and conforms to the surface thereof Support member 40 has a first portion 42, a second portion 44, and a third portion 46. First portion 42, second portion 44, and third portion 46 each have a distal end 52, 54, and 56 respectively. In addition, first portion 42, second portion 44, and third portion 46 each have a proximal end 62, 64, and 66 respectively.

First portion 42 of support member 40 is disposed proximate distal end 14 of inner tubular member 30 and is comprised of at least one filament 100 which is circumferentially disposed about inner tubular member 30. At least one filament 100 generally conforms to the shape of outer surface 36 of inner tubular member 30 and forms a plurality of turns 102 in a helical pattern.

In the embodiment of FIG. 2, at least one filament 100 follows a generally helical path. Also in the embodiment of FIG. 2, one filament 100 is illustrated. Those of skill in the art will appreciate, however, that two or more filaments could be circumferentially disposed about inner tubular member 30 without departing from the spirit or scope of the present invention. For example, two filaments 100 could be wound around inner tubular member 30, each filament following a generally helical path, such that the two filaments create a double helix.

A ring 70 is circumferentially disposed about outer surface 36 of inner tubular member 30 proximate the distal end thereof. In a presently preferred embodiment, ring 70 is comprised of a radiopaque material. In this presently preferred embodiment, ring 70 produces a relatively bright image on a fluoroscopy screen during a medical procedure. This relatively bright image aids the user of catheter 10 in determining the location of distal end 14 of elongate shaft 12. A number of radiopaque materials are acceptable for use in fabricating ring 70. Acceptable materials included gold, platnium, and a plastic material loaded with a radiopaque filler.

In the embodiment of FIG. 2, a distal portion 104 of at least one filament 100 is disposed between outer surface 36 of inner tubular member 30 and radiopaque ring 70. Placing distal portion 104 of filament 100 in this position has the advantage of retaining distal portion 104 of filament 100 while the remainder of filament 100 is wound around inner tubular member 30.

Second portion 44 of support member 40 is circumferentially disposed about inner tubular member 30, with its distal end 54 proximate proximal end 62 of first portion 42 of support member 40. Second portion 44 of support member 40 is comprised of a first layer 82, a second layer 84, and a third layer 86. Each layer 82, 84, and 86 is comprised of a plurality of turns 92, 94, and 96, respectively. Turns 92, 94, and 96 are formed of filaments 112, 114, and 116, respectively. In a presently preferred embodiment, filaments 100, 112, 114, and 116 are all coextensive.

Third portion 46 of support member 40 is comprised of a plurality of turns 122 formed by at least one filament 120. In a presently preferred embodiment, filament 120 is coextensive with both filaments 100, 112, 114 and 116. Third portion 46 of support member 40 is disposed with its distal end 56 proximate proximal end 64 of second portion 44.

In a presently preferred embodiment, elongate shaft 12 includes a flare 22 disposed proximate proximal end 16 thereof. Hub 26 may be formed over proximal end 16 of elongate shaft 12 as shown in FIG. 1. In a presently preferred embodiment, hub 26 is formed using an overmolding process. Also in a presently preferred embodiment, support member 40 is formed of a single filament 200. In this presently preferred embodiment, filament 200 is comprised of filaments 100, 112, 114, 116, and 120, all of which are coextensive. In this presently preferred embodiment, filament 200 includes a distal end 202 and a proximal end 204. In this presently preferred embodiment, it is unlikely that distal end 202 of filament 200 will protrude through the outer layer of catheter 10 since the distal portion of filament 200 is retained by ring 70, as described above. Likewise, it is unlikely that proximal end 204 of filament 200 will protrude from catheter 10, since hub 26 is formed over proximal end 16 of elongate shaft 12.

FIG. 2 is an enlarged, partial cross-section illustrating second portion 44 of support member 40. As shown in FIG. 2, second layer 84 of second portion 44 of support member 40 overlays first layer 82. Likewise, third layer 86 of second portion 44 of support member 40 overlays second layer 84. Referring again to FIG. 2, it can be appreciated that an outer layer 190 overlays both support member 40 and inner tubular member 30. In a presently preferred embodiment, the material of outer layer 190 fills in any interstitial spaces in support member 40. Also in a presently preferred embodiment, outer layer 190 is comprised of a distal portion 192, a middle portion 194, and a proximal portion 196.

In the embodiment of FIG. 2, the proximal end of distal portion 192 of outer layer 190 has been fused to the distal end of middle portion 194. Likewise, the proximal end of middle portion 194 of outer layer 190 has been fused to the distal end of proximal portion 196. In this presently preferred embodiment, distal portion 192, middle portion 194, and proximal portion 196 combine to form an outer layer 190 which is substantially continuous.

As shown in FIG. 2, proximal portion 196 of outer layer 190 has an outer diameter A, and distal portion 192 has an outer diameter D. In the embodiment of FIG. 2, middle portion 194 of outer layer 190 includes a first outer diameter B substantially equal to outer diameter A of proximal portion 196 and a second outer diameter C substantially equal to outer diameter D of distal portion 192. Middle portion 194 also includes a taper 98 extending between outer diameter B and outer diameter C of middle portion 194.

In the embodiment of FIG. 2, distal end 54 of second portion 44 of support member 40 is disposed proximate taper 98 of middle portion 194 of outer layer 190. Those of skill in the art will appreciate that other embodiments are possible without deviating from the spirit or scope of the present invention. For example, distal end 54 of second portion 44 of support member 40 may be disposed proximal to taper 98 of middle portion 194 of outer layer 190.

Also in the embodiment of FIG. 2, outer diameter A of proximal portion 196 of outer layer 190 is large enough to substantially cover layers 82, 83, and 84 of second portion 44 of support member 40. Likewise, outer diameter D of distal portion 192 of outer layer 190 is large enough to substantially cover first portion 42 of support member 40. In a presently preferred embodiment, outer diameter D of distal portion 192 is smaller than outer diameter A of proximal portion 196. It may be appreciated that the single layer construction of first portion 42 of support member 40 facilitates having an outer diameter D of distal portion 192 which is smaller than outer diameter A of proximal portion 96.

As described previously, in a presently preferred embodiment, distal end 202 of filament 200 is retained by ring 70, and proximal end 204 of filament 200 is disposed within hub 26 of catheter 10. In this presently preferred embodiment, diameters A and D do not need to be enlarged to prevent distal ends 202 and 204 from protruding out of catheter 10.

In the embodiment of FIG. 2, the plurality of turns 102 forming first portion 42 of support member 40 are disposed at a first pitch 152. Also in the embodiment of FIG. 2, the turns 82, 84, and 86 of second portion 44 of support member 40 are disposed at a second pitch 154 different than first pitch 152. Finally, in the embodiment of FIG. 2, turns 122 of third portion 46 of support member 40 are disposed at a third pitch 156. In a presently preferred embodiment, pitches 152, 154, and 156 of support member 40 may be selected to impart desired performance characteristics upon catheter 10. For example, third pitch 156 may be relatively coarse to so that it does not hinder the formation of flare 22.

In a presently preferred embodiment, distal end 52 of first portion 42 of support member 40 is disposed proximate distal end 14 of elongate shaft 12. An atraumatic tip 150 is formed of inner tubular member 30 and outer layer 190. In the embodiment of FIG. 2, atraumatic tip 150 is disposed distally of distal portion 52 of first portion 42 of support member 40. In this presently preferred embodiment, atraumatic tip 150 has a level of flexibility which makes it unlikely to damage the blood vessels of a patient.

As described previously, filaments 100, 112, 114, 116, and 120 of support member 40 are coextensive in a presently preferred embodiment. In a presently preferred embodiment, filaments 100, 112, 114, 116, and 120 comprise metal wire. In a presently most preferred embodiment, filaments 100, 112, 114, 116, and 120 are comprised of stainless steel wire. Those of skill in the art will appreciate that filaments 100, 112, 114, 116, and 120 may be comprised of other materials without deviating from the spirit or scope of the present invention. Those of skill in the art will also appreciate that filaments 100, 112, 114, 116, and 120 may be comprised of metallic or non-metallic materials. Examples of materials which may be suitable in some applications include: nickel titanium alloy, nylon, KEVLAR, and carbon fibers.

Also in a presently preferred embodiment, outer layer 190 is comprised of polyether block amide (PEBA). Polyether block amide is commercially available from Atochem Polymers of Birdsboro, Pa., under the trade name PEBAX. In a presently most preferred embodiment, distal portion 192, middle portion 194, and proximal portion 196 of outer tubular layer are comprised of a PEBA polymer having durometers of about 35, 63, and 72 respectively.

Outer layer 190 may be comprised of other materials without departing from the spirit of scope of this invention. Examples of materials which may be suitable in some applications include polyethylene (PE), polypropylene (PP), polyvinylchloride (PVC), polyurethane, and polytetrafluoroethylene (PTFE). It should be understood that additives, loading agents, or fillers may be added to the material of outer layer 190 without deviating from the spirit or scope of the present invention. These additional materials may include color pigments, radiopaque materials, lubricants, or fillers.

FIG. 3 is a plan view of an assembly including inner tubular member 30 and a filament 300. A ring 70 is circumferentially disposed about outer surface 36 of inner tubular member 30 proximate its distal end 38. A distal portion 301 of filament 300 is disposed between outer surface 36 of inner tubular member 30 and radiopaque ring 70.

First portion 42 of support member 40 is disposed proximate distal end 38 of inner tubular member 30 and is comprised of at least one filament 300. Filament 300 is circumferentially disposed about inner tubular member 30 and generally conforms to the shape of outer surface 36. In the embodiment of FIG. 3, filament 300 follows a generally helical path and forms a plurality of turns 302.

Those of skill in the art will appreciate, however, that two or more filaments could be circumferentially disposed about inner tubular member 30 without departing from the spirit or scope of the present invention. If two filaments were utilized, for example, they would form a double helix.

Turns 302 of first portion 42 are disposed at a first pitch 152 and combine to form the first portion 42 of a support member 40. In a presently preferred embodiment, turns 302 are disposed at a first pitch 152 of between about 0.020 inches per turn and 0.002 inches per turn. In a presently most preferred embodiment, turns 302 are disposed at a first pitch 152 of about 0.006 inches per turn.

As shown in FIG. 3, filament 300 extends beyond first portion 42 of support member 40 to form the first layer 82 of a second portion 44 of support member 40. Filament 300 is circumferentially disposed about inner tubular member 30 and follows a generally helical path, forming a plurality of turns 304. Turns 304 of second portion 44 are disposed at a second pitch 154. In a presently preferred embodiment, turns 304 are disposed at a second pitch 154 of between about 0.050 inches per turn and 0.005 inches per turn. In a presently most preferred embodiment, turns 304 are disposed at a second pitch 154 of about 0.018 inches per turn.

In the embodiment of FIG. 3, first pitch 152 is generally finer than second pitch 154. Those of skill in the art will recognize that a number of values may be used for first pitch 152 and second pitch 154 without deviating from the spirit and scope of the present invention. For example, embodiments of the present invention have been envisioned in which first pitch 152 and second pitch 154 are substantially equal.

FIG. 4 is a plan view of the assembly of FIG. 3, in which a second layer 84 has added to second portion 44 of support member 40. Second layer 84 is comprised of a plurality of turns 306 which overlay first layer 82 of second portion 44 of support member 40. Turns 306 are formed by filament 300 which is disposed along a generally helical path overlaying first layer 82 of second portion 44 of support member 40.

FIG. 5 is a plan view of the assembly of FIG. 4, in which a third layer 86 has added to second portion 44 of support member 40. Third layer 86 is comprised of a plurality of turns 308 which overlay second layer 84 of second portion 44 of support member 40. Turns 308 are formed by filament 300 which is disposed along a generally helical path overlaying second layer 84 of second portion 44 of support member 40.

In the assembly of FIG. 5, filament 300 extends beyond second portion 44 of support member 40 to form a third portion 46 of support member 40. Filament 300 is circumferentially disposed about inner tubular member 30 and follows a generally helical path, forming a plurality of turns 310. Turns 310 of third portion 46 are disposed at a third pitch 156. In a presently preferred embodiment, third pitch 156 is generally more coarse than first pitch 152 and second pitch 154.

FIG. 6 is a plan view of the assembly of FIG. 5, in which portions 192, 194, and 196 forming outer layer 190 of elongate shaft 12 are circumferentially disposed over support member 40 and inner tubular member 30.

Having thus described the figures, a method of manufacturing catheter 10 may now be described with reference thereto. A method in accordance with the present invention typically begins with the step of temporarily or permanently securing distal portion 192 of filament 300 to inner tubular member 30 proximate its distal end. In a presently preferred method, distal portion 192 of filament 300 is secured by ring 70. As seen in FIG. 3, ring 70 is circumferentially disposed about inner tubular member 30 proximate its distal end 38, while distal portion 192 of filament 300 is disposed between ring 70 and outer surface 36 of inner tubular member 30. In a presently preferred method in accordance with the present invention, a distal end 350 of filament 300 is tied off. In this presently preferred embodiment, a location for tying off distal end 350 of filament 300 is provided as part of an apparatus for winding filament 300.

Those of skill in the art will appreciate that other methods of fixing distal portion 192 of filament 300 to inner tubular member 30 may be used without deviating from the spirit or scope of the present invention. Methods which may be acceptable in some applications include welding, gluing, and tying. The use of adhesive tape or mechanical fasteners may also be applicable to some embodiments of the present invention.

Filament 300 may be wound around inner tubular member 30 following a generally helical path to form a plurality of turns. First portion 42 of support member 40 is comprised of a plurality of turns 302. In a presently preferred embodiment, turns 302 of first portion 42 of support member 40 are wound at a first pitch 152.

In a presently preferred method, filament 300 is wound beyond first portion 42 to form first layer 82 of second portion 44 of support member 40. In a presently preferred embodiment, turns 304 of second portion 44 are wound at a second pitch 154. Those of skill in the art will appreciate that first portion 42 and second portion 44 may be wound at the same pitch without deviating from the spirit and scope of the present invention.

In the embodiment of FIG. 3, the winding of filament 300 proceeds in a proximal direction. When the path of filament 300 reaches a desired point, the direction of winding travel is reversed so that filament 300 begins forming turns 306 which overlay turns 304 of first layer 82. In this manner, second layer 84 of second portion 44 of support member 40 is formed. As shown in FIG. 3, second layer 84 is comprised of turns 306 formed from filament 300.

The winding of filament 300 proceeds in a distal direction until the path of filament 300 reaches distal end 54 of second portion 44 of support member 40. At this point, the direction of winding travel is reversed so that filament 300 begins forming turns 308 which overlay turns 306 of second layer 84. In this manner, third layer 86 of second portion 44 of support member 40 is formed.

Third portion 46 of support member 40 may be formed by proceeding to wind filament 300 along a generally helical path in a proximal direction beyond proximal end 65 of second portion 44 of support member 40. After the formation of third portion 46 is complete, filament 300 may be cut off at a desired location, to separate it from the spool it was dispensed from.

The steps involved in forming outer layer 190 of elongate shaft 12 are best illustrated in FIG. 6. In a presently preferred method, proximal portion 196, middle portion 194, and distal portion 192 of outer layer 190 are all slid over support member 40 and inner tubular member 30. After positioning, portions 192, 194, and 196 are all circumferentially disposed over support member 40 and inner tubular member 30, as shown in FIG. 6.

A sleeve 360 (not shown) may then be placed over the assembly. In a presently preferred method, sleeve 360 is comprised of polytetrafluoroethylene (PTFE). PTFE is preferred because it provides a substantially non-stick surface. In a presently most preferred embodiment, sleeve 360 is comprised of PTFE shrink tubing. Suitable PTFE shrink tubing is commercially available Zeus Industries of Orangeburg, S.C., and Raychem Corporation of Menlo Park, Calif.

After placing sleeve 360 in the desired position, heat may be applied to sleeve 360 causing it to shrink. After shrinking, sleeve 360 substantially conforms to the outer surfaces of proximal portion 196, middle portion 194, and distal portion 192. A number of methods may be used to heat sleeve 360, including convection heating, radiation heating, and heating by conduction. In a presently preferred embodiment, sleeve 360 is heated by directing a flow of hot air from a hot air gun so that it impinges on sleeve 360. Hot air guns suitable for this application are commercially available from Leister Elektro-Geratebau of Lucerne, Switzerland.

After shrinking, sleeve 360 serves to retain the position of proximal portion 196, middle portion 194, and distal portion 192. Sleeve 360 also applies radially constrictive pressure to the outer surfaces of proximal portion 196, middle portion 194, and distal portion 192. It should be understood that the steps of overlaying sleeve 360 over the assembly and shrinking sleeve 360 may be omitted without deviating from the spirit and scope of the present invention. Methods in accordance with the present invention have been envisioned which do not utilize sleeve 360. Methods in accordance with the present invention have also been envisioned in which the assembly is heated during subsequent steps, and the step of applying heat to sleeve 360 is omitted.

In a presently preferred method in accordance with the present invention, distal portion 192, middle portion 194, and proximal portion 196 are heated to a temperature near their melting point, causing them all to fuse together forming outer layer 190. The elevated temperature also causes outer layer 190 to be securely bonded to support member 40 and inner tubular member 30. In a presently preferred embodiment, the material of outer layer 190 fills in any interstitial spaces in support member 40.

A number of methods may be used to heat the assembly, including convection heating, radiation heating, and heating by conduction. An example of heating with radiant energy is directing infrared energy from an infrared heat source at the assembly. Infrared energy sources suitable for this process are commercially available from Research Incorporated of Minnetonka, Minn. A second example of heating with radiant energy is exposing the regions to be heated to radio frequency energy.

An example of heating with convection includes placing the assembly being heated in a temperature chamber. Temperature chambers suitable for this process are commercially available from Thermotron Corporation of New Holland, Mich.

An example of heating with conduction is placing a heated tool in direct contact with the assembly. Suitable heated tools may be comprised of a number of materials including stainless steel. Electric heaters suitable for heating a heated tool are commercially available from Watlow Incorporated of St. Louis, Mo.

Having formed outer layer 190, the assembly may be allowed to cool. To speed cooling, the assembly may be submersed in a relatively cool fluid. Examples of fluids which may be suitable for some applications include water and air. In one method in accordance with the present invention, a temperature chamber with both heating and cooling capabilities is utilized. This temperature chamber is capable of producing an elevated temperature environment for heating and a low temperature environment for cooling. Temperature chambers with this capability are commercially available from Thermotron Corporation of New Holland, Mich. A flow of relatively cool air may also be directed at the assembly to speed cooling. Cold air generators suitable for this purpose are commercially available from ITW Vortec of Cincinnati, Ohio, and Exair Corporation of Cincinnati, Ohio.

After the assembly has cooled, sleeve 360 may be removed. This may be accomplished by scoring sleeve 360 with a cutting tool, and peeling it away from outer layer 190. In a presently preferred method, sleeve 360 is comprised of polytetrafluoroethylene (PTFE). PTFE is preferred because it provides a substantially non-stick surface. This substantially non-stick surface aids in the removal of sleeve 360 from outer layer 190.

In one method in accordance with the present invention, a mandrel is placed in lumen 20 of inner tubular member 30. If a mandrel has been used, it may also be removed after the assembly has cooled. It should be understood that steps may be omitted from this process without deviating from the spirit or scope of the invention. For example, alternate methods have been envisioned, in which the use of sleeve 360 is not required.

Having thus described the preferred embodiments of the present invention, those of skill in the art will readily appreciate that yet other embodiments may be made and used within the scope of the claims hereto attached.

Numerous advantages of the invention covered by this document have been set forth in the foregoing description.

It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A catheter comprising:
    an inner tubular member having an outer surface, a proximal end, a distal end, and a lumen extending therethrough;
    a support member overlaying the inner tubular member and conforming to the outer surface thereof, the support member having a first portion, a second portion, and a third portion, each portion having a distal end and a proximal end;
    a radiopaque ring disposed about the outer surface of the inner tubular member and positioned proximate the distal end thereof;
    the first portion of the support member comprising a single layer arranged with a plurality of turns, the turns being disposed at a first pitch;
    the distal end of the first portion of the support member being disposed proximate the radiopaque ring;
    a distal portion of the at least one filament being disposed between the inner tubular member and the radiopaque ring;
    the distal end of the second portion of the support member being disposed proximate the proximal end of the first portion of the support member;
    the second portion of the support member comprising a first layer, a second layer, and a third layer, each layer comprising a plurality of turns formed by the at least one filament;
    wherein the second layer of the second portion of the support member overlays the first layer thereof, and the third layer of the second portion of the support member overlays the second layer thereof;
    the turns of the second portion of the support member being disposed at a second pitch;
    the third portion of the support member comprising a single layer arranged with a plurality of turns;
    the turns of the third portion of the support member being disposed at a third pitch;
    the distal end of the third portion of the support member being disposed proximate the proximal end the second portion of the support member;
    an outer layer overlaying and bonded to both the support member, and the inner tubular member;
    the outer layer including a proximal portion, a middle portion, and a distal portion, each portion having at least one outer diameter;
    the middle portion of the outer layer including a first outer diameter substantially equal to the outer diameter of the proximal portion, a second outer diameter substantially equal to the outer diameter of the distal portion, and a taper extending between the first outer diameter and the second outer diameter; and
    the outer diameter of the proximal portion of the outer layer being larger than the outer diameter of the distal portion of the outer layer.

2. The catheter of claim 1, wherein the inner tubular member is comprised of an inner layer and an outer layer.

3. The catheter of claim 1, wherein the inner tubular member is comprised of an inner layer and an outer layer, the inner layer being comprised of a fluoropolymer, and the outer layer being comprised of polyether block amide.

4. The catheter of claim 1, wherein the at least one filament of the first portion of the support member and the at least one filament of the second portion of the support member are coextensive.

5. The catheter of claim 1, wherein the at least one filament of the first portion of the support member, the at least one filament of the second portion of the support member, and the at least one filament of the third portion are all coextensive.

6. The catheter of claim 1, wherein the at least one filament is comprised of a metal wire.

7. The catheter of claim 1, wherein the at least one filament has a circular cross-section with an outer diameter of 0.00145 inches.

8. The catheter of claim 1, wherein the first pitch is finer than the second pitch.

9. The catheter of claim 1, wherein the first pitch is finer than the second pitch, and the second pitch is finer than the third pitch.

10. The catheter of claim 1, wherein the first pitch is one turn every 0.006 inches.

11. The catheter of claim 1, wherein the second pitch is one turn every 0.018 inches.

12. The catheter of claim 1, wherein the third pitch is one turn every 0.054 inches.

13. The catheter of claim 1, wherein the distal portion of the outer layer has a durometer lower than that of the middle portion of the outer layer.

14. The catheter of claim 1, wherein the distal portion of the outer layer has a durometer lower than that of the middle portion of the outer layer, and the middle portion of the outer layer has a durometer lower than that of the proximal portion of the outer layer.

15. The catheter of claim 1, wherein the outer layer is comprised of polyether block amide.

16. The catheter of claim 1, wherein the proximal portion, the middle portion, and the distal portion of the outer layer are each comprised of polyether block amide having different durometers.

17. The catheter of claim 1, wherein the distal portion of the outer layer is comprised of polyether block amide having a durometer of 35 on the Shore D scale.

18. The catheter of claim 1, wherein the middle portion of the outer layer is comprised of polyether block amide having a durometer of 63 on the Shore D scale.

19. The catheter of claim 1, wherein the proximal portion of the outer layer is comprised of polyether block amide having a durometer of 72 on the Shore D scale.

20. The catheter of claim 1, further including a coating overlaying the outer layer.

21. The catheter of claim 1, further including an coating overlaying the outer layer, the coating comprising a hydrophilic, lubricious material.

* * * * *